(12) United States Patent
Mueller (10) Patent No.: US 9,861,535 B2
(45) Date of Patent: Jan. 9, 2018

(54) TAMPON FOR DAYS BETWEEN MENSTRUATION

(71) Applicant: Ruggli Projects AG, Hagendorn (CH)

(72) Inventor: Peter Mueller, Zurich (CH)

(73) Assignee: Ruggli Projects AG, Hagendorn (CH)

( * ) Notice: Subject to any disclaimer, the term of this patent is extended or adjusted under 35 U.S.C. 154(b) by 51 days.

(21) Appl. No.: 14/589,488

(22) Filed: Jan. 5, 2015

(65) Prior Publication Data

US 2015/0164702 A1 Jun. 18, 2015

Related U.S. Application Data

(63) Continuation of application No. PCT/EP2013/064277, filed on Jul. 5, 2013.

(30) Foreign Application Priority Data

Jul. 6, 2012 (AT) .................................. A 751/2012

(51) Int. Cl.
*A61F 13/64* (2006.01)
*A61F 13/20* (2006.01)
*A61F 13/15* (2006.01)

(52) U.S. Cl.
CPC .... *A61F 13/2051* (2013.01); *A61F 13/15203* (2013.01); *A61F 13/202* (2013.01); *A61F 13/2002* (2013.01); *A61F 13/206* (2013.01); *A61F 13/2022* (2013.01); *A61F 13/2034* (2013.01); *A61F 13/2042* (2013.01); *A61F 13/2057* (2013.01); *A61F 13/2074* (2013.01); *A61F 13/64* (2013.01); *A61F 2013/15365* (2013.01); *A61F 2013/15471* (2013.01)

(58) Field of Classification Search
CPC ............ A61F 13/15203; A61F 13/2002; A61F 13/202; A61F 13/2022; A61F 13/2034; A61F 13/2051; A61F 2013/15365; A61F 2013/15471
See application file for complete search history.

(56) References Cited

U.S. PATENT DOCUMENTS

| | | |
|---|---|---|
| 2,499,414 A | 3/1950 | Rabell |
| 2,761,449 A | 9/1956 | Bletzinger |
| 2,849,000 A | 8/1958 | Lewing |
| 3,320,956 A | 5/1967 | Steiger |

(Continued)

FOREIGN PATENT DOCUMENTS

| | | |
|---|---|---|
| CH | 248634 A | 5/1947 |
| DE | 1 187 345 B | 2/1965 |

(Continued)

OTHER PUBLICATIONS

International Search Report of PCT/EP2013/064277, dated Sep. 16, 2013.

(Continued)

*Primary Examiner* — Peter S Vasat
(74) *Attorney, Agent, or Firm* — Collard & Roe, P.C.

(57) ABSTRACT

A tampon with an absorbent body of which at least a part of its volume is made from an absorbent material and having a middle part, a distal end and a proximal end, and which is connected to an extraction device. The volume of absorbent material in such a tampon is designed to absorb between 0.5 g and 4 g, preferably 3.5 g, of liquid.

24 Claims, 5 Drawing Sheets

(56) References Cited

U.S. PATENT DOCUMENTS

| | | | |
|---|---|---|---|
| 4,374,522 | A | 2/1983 | Olevsky |
| 5,813,102 | A | 9/1998 | Leutwyler et al. |
| 6,889,409 | B2 | 5/2005 | Friese et al. |
| 7,014,637 | B1 | 3/2006 | Denti et al. |
| 7,112,192 | B2 * | 9/2006 | Hasse .................. A61F 13/206 604/385.17 |
| 7,144,391 | B1 | 12/2006 | Kreutz et al. |
| 7,867,209 | B2 * | 1/2011 | Jorgensen ......... A61F 13/15203 604/330 |
| 7,967,803 | B2 | 6/2011 | Van Ingelgem et al. |
| 8,864,732 | B2 | 10/2014 | Van Ingelgem et al. |
| 2002/0151859 | A1 * | 10/2002 | Schoelling ......... A61F 13/2051 604/385.17 |
| 2003/0176845 | A1 * | 9/2003 | Kollwitz ............. A61F 13/2031 604/385.17 |
| 2005/0193536 | A1 * | 9/2005 | Ingelgem .............. A61F 13/206 28/118 |
| 2007/0073257 | A1 * | 3/2007 | Buck ................... A61F 13/2051 604/385.18 |
| 2008/0132868 | A1 * | 6/2008 | Jorgensen ......... A61F 13/15203 604/385.17 |
| 2008/0221502 | A1 * | 9/2008 | Binner ................ A61F 13/2085 604/11 |
| 2010/0036309 | A1 * | 2/2010 | Jorgensen, Jr. ......... A61F 13/84 604/15 |
| 2010/0299897 | A1 * | 12/2010 | Schoelling .......... A61F 13/2051 28/120 |
| 2012/0089111 | A1 * | 4/2012 | Magnusson ......... A61F 13/2051 604/385.18 |

FOREIGN PATENT DOCUMENTS

| | | |
|---|---|---|
| DE | 1 491 169 C3 | 1/1974 |
| DE | 37 39 163 A1 | 6/1989 |
| DE | 43 04 505 A1 | 8/1994 |
| DE | 198 25 877 C1 | 11/1999 |
| DE | 103 06 678 A1 | 8/2004 |
| DE | 203 20 992 U1 | 8/2005 |
| DE | 20 2006 000 746 U1 | 6/2006 |
| DE | 60 2004 003 888 T2 | 8/2007 |
| DE | 10 2008 020 640 A1 | 11/2009 |
| DE | 20 2009 000 983 U1 | 7/2010 |
| EP | 0 422 660 A1 | 4/1991 |
| EP | 0 611 562 A1 | 8/1994 |
| WO | 02/17844 A2 | 3/2002 |

OTHER PUBLICATIONS

EDANA regulation Reference No. 350.0-02, "Tampons absorbency," Feb. 2002, pp. 215-221.

* cited by examiner

TAMPON FOR DAYS BETWEEN MENSTRUATION

CROSS REFERENCE TO RELATED APPLICATIONS

Applicant claims priority under 35 U.S.C. §119 of Austrian Application No. A 751/2012 filed Jul. 6, 2012. Applicant also claims priority and this application is a continuation under 35 U.S.C. §120 of International Application No. PCT/EP2013/064277 filed Jul. 5, 2013, which claims priority under 35 U.S.C. §119 of Austrian Application No. A 751/2012 filed Jul. 6, 2012. The International Application under PCT article 21(2) was not published in English. The disclosures of the aforesaid International Application and Austrian Application are incorporated herein by reference.

The invention relates to a tampon for days between menstruation days, having at least an absorbent body, at least a part of the volume of which is made from an absorbent material, and having a middle part, a proximal end and a distal end and an extraction means connected to the tampon.

In the past, tampons have been used during menstruation instead of sanitary pads. The disadvantage of these pads is that women are often sensitive about pads or have an allergic reaction to them or find pads unpleasant.

Conventional tampons known from the prior art are used in particular as menstruation tampons and are inserted via a body orifice, in particular the vagina, and the tampon can be positioned in this body orifice. Such tampons are known from EP 0 422 660, EP 0 611 562, U.S. Pat. No. 2,499,414, DE 60 2004 003 888, DE 1 9825 877A, DE 37 39 163A, DE 4 304 505A, CH 248 634A, DE 1 187 345A, DE 20 320 992A, DE 10 306 678A, DE 10 2008 020 640 A, DE 20 2006 000 746 U1, DE 20 2009 000 983U, for example.

Conventional tampons known from the prior art come in in the following dimensions and sizes. The length of the conventional tampon is between 40 mm and 70 mm and the diameter is greater than 11 mm, for example.

The conventional tampon may be made from absorbent material, from highly compressed absorbent material and/or from absorptive material. To enable it to be removed from the body orifice, it has an extraction means, e.g. a retraction cord.

The conventional tampon may have markings on its surface and it may be made in different colors. The tampon may also be made with a chemical indicator, which changes color in the presence of specific illnesses, such as anemia, diabetes, hepatitis A, B or C and HIV.

Due to the dimensions of the conventional tampon, this tampon is not used every day but rather on menstruation days only, and due to the high quantity of fluid generated during this time undergoes a significant increase in weight.

Documents DE 1 491 169 C and U.S. Pat. No. 2,761,449 A disclose tampons with an absorption capacity of between 4.4 and 6 g and between 10.85 and 18.40 g.

Tampons are also known from U.S. Pat. No. 2,849,000A which have an absorption capacity of 6 to 8 g.

A so called "Junior tampon" with an absorption capacity of less than 6 g is known from WO02/17844A2, for example Another known approach to absorbing body fluids from the vagina on days between menstruation days, including in particular during the menopause, is to use panty liners. In the case of many women, however, these lead to complaints and irritation and can therefore not be used in many cases.

Accordingly, the underlying objective of this invention is to propose an everyday tampon or a tampon which can be used between individual menstruation phases, which offers good properties in terms of comfort during use and which preferably can be manufactured inexpensively. As proposed by this invention, the objective is achieved due to the fact that the tampon for days between menstruation times with a volume of an absorbent material capable of absorbing a liquid quantity of between 0.5 g and 4 g preferably 3.5 g and the absorbent body has a length shorter than 40 mm, preferably a length of between 40 and 10 mm or between 38 and 30 mm.

The advantages of such an everyday tampon or such a tampon reside in the fact that this tampon can be worn invisibly and in addition can reduce odors or can even have the effect of reducing odors. Furthermore, this cannot lead to irritation in the region of the vagina entrance. Another advantage is the fact that this tampon can be used whilst playing sports and above all when swimming, thereby offering women a high degree of independence in terms of clothing. Another advantage is that when the tampon is in the inserted state and also after absorbing fluid, the musculature in the region of the vagina exerts only a slight radial and vertical force, thereby resulting in a high degree of wearing comfort suitable for daily use of such a tampon.

An additional improvement can be achieved if the tampon and/or absorbent body has a length shorter than 40 mm, preferably a length of between 40 and 10 mm or between 38 and 30 mm, as a result of which the expansion and pressure of the tampon on the uterus is reduced, thereby preventing tightening and damming of the outlet orifice of the uterus, which can cause considerable discomfort.

Another possible embodiment is proposed in which the absorbent body is made from an absorbent material throughout its entire volume, thereby enabling the dimensions of the diameter of a tampon and the quantity of fluid which can be absorbed to be optimized.

Based on another advantageous embodiment, the absorbent material is made from a fibrous material, as a result of which the droplets of liquid can adhere to the individual fibers, thereby resulting in a high absorption capacity of the absorbent body of an everyday tampon or tampon.

However, it is also of advantage if the absorbent material is a compressed fibrous material, because this makes handling of the tampon easier, especially inserting and removing the tampon.

For an everyday tampon or tampon, it is also of advantage if the volume of the absorbent material is designed to absorb a liquid quantity of between 0.5 g and 4 g, preferably 3.5 g. This prevents a high suction effect on the mucous membranes and also makes it easier to remove the everyday tampon or tampon if there is only a small amount of liquid. This also makes it easier to prevent or significantly reduces the risk of a toxic shock syndrome (TSS).

It is also of advantage if a maximum diameter of the absorbent body or a bounding volume surrounding the absorbent body is at most 10 mm, preferably having a value of between 2 and 10 mm. This slim diameter also reduces the force of the musculature of the vagina, bringing better comfort. In addition, the slimmer diameter puts less pressure on the sphincter musculature of the bladder.

It is also of advantage if at least the middle part of the absorbent body or an bounding volume surrounding it is cylindrical in shape, thereby resulting in a uniform contact with the mucous membranes of the vagina.

However, it may prove to be of advantage if at least the middle part of the absorbent body or a bounding volume surrounding it is of a conical or frustoconical shape because this makes it easier to insert the everyday tampon or tampon.

Based on another embodiment, the cone or truncated cone extends continuously from the proximal end to the distal end, thereby making it easier to remove the everyday tampon or tampon.

Another option is one where a core region of fibrous material is disposed inside at least the middle part of the absorbent body, which is designed to absorb a smaller liquid quantity for the same volume than the material of the absorbent body. This means that, in spite of bigger diameters of the tampon which might be desired or needed for different anatomical designs, the suction effect and degree of liquid absorption can be more easily adapted to the requisite requirements, especially in the absorbent body.

A core region made from a material designed to absorb a smaller liquid quantity than the material of the absorbent body or repel liquid for the same volume may also be disposed inside at least the middle part of the absorbent body. This enables the liquid quantity to be absorbed to be fixed exclusively on the basis of the shape and volume of the absorbent body.

However, it is also of advantage if the fibrous material of the absorbent body has a total weight of at most 2 g, preferably 1.7 g, and a minimum weight of 0.5 g, preferably 0.2 g, because this means that the weight of the tampon can be kept so low, even when filled with liquid, that the problems outlined in the preceding paragraph can be reduced or prevented.

It is advantageously possible to adapt the suction effect and also the liquid absorption capacity of the tampon by providing the absorbent body with a cavity, in which case an opening to this cavity is disposed in the region of its distal end. This makes it possible to produce a standard absorbent body which, by inserting different core regions with a different three-dimensional shape, but in particular with a different diameter regardless of whether it remains constant across the entire length or varies, can be used to obtain different external dimensions of the tampon whilst nevertheless retaining the same capacity to absorb liquid and the suction effect induced as a result.

It is also of advantage if the extraction means is connected to the absorbent body and/or core region of the tampon because this enables safe removal of the tampon from the body cavity.

Based on another embodiment, an outer surface of the absorbent body or middle part is at least partially provided with a casing, for example made from a nonwoven. This rules out or reduces a loss of fiber or the possibility of fibers adhering to the mucous membranes.

However, it would also be possible for only the proximal end and the middle part to be provided with an at least partially liquid-permeable casing, for example made from a nonwoven. This makes it easier to apply the nonwoven and prevents any loss of fiber above all in those areas where there is virtually full contact with the mucous membrane.

In this connection, it is also of advantage if the casing is provided in the form of a net or a perforated film.

It is of advantage if the absorbent fibrous material is made from one or more materials such as rayon, cotton, cellulose, cellulose wadding, layered tissue, sphagnum, bamboo or chemically reinforced, modified or cross-linked cellulose fibers. This fibrous material has a high hygroscopy and enables large quantities of liquid to adhere to the external faces of the fibers and is biologically neutral.

However, it would also be possible to use absorbent fibrous materials made from one or more of the following synthetic materials, such as polyester fibers, polyolefin fibers, absorbent foams, absorbent sponges, absorbent polymers, capillary channel fibers, synthetic fibers, predominantly open-celled flexible polyurethane foam or fibers or filaments of rayon or a structure type of the crystal modification of cellulose II.

For an everyday tampon or tampon, it is also of advantage if the core region of the absorbent body is disposed inside a bounding circle or bounding cylinder with preferably a same diameter (21) across its length, which is preferably smaller than 4 mm or between 4 mm and 1 mm. This results in a more stable absorbent body. In this respect, it is of particular advantage if fibrous material in the core region of the absorbent body is compressed to a greater degree than in the other regions of the absorbent body. The fact that the entire body is more stable also makes handling easier.

It is of advantage if the everyday tampon or tampon is round or rounded at the proximal end. This makes it easier to introduce into a body opening. This is of advantage for tampon users (e.g. young girls) and women with a dry vagina.

In another advantageous embodiment, the absorbent body is provided with recesses and grooves extending in the longitudinal direction thereof and/or the recesses and grooves are wave-shaped in the direction of the longitudinal mid-axis of the absorbent body, preferably extending with a constant height of amplitude, thereby increasing the surface area of the tampon. This enables more body fluid to be absorbed, for example, because the body can discharge different quantities of body fluid between consecutive menstruation phases. These grooves are also of advantage if using insertion aids for the everyday tampon or tampon.

An even larger surface area for absorbing liquid can be obtained if the grooves and recesses extend in a spiral pattern or helically.

Another advantage can be obtained if several grooves and recesses are distributed in the circumferential direction around the absorbent body. This also increases the surface area of the tampon so that more body fluid is absorbed because the body can discharge different quantities of body fluid between menstruation phases. For women with a heavier flow, this offers better hygiene than a panty liner. These grooves are likewise of advantage if using insertion aids for everyday tampons or tampons.

Another advantage of using the everyday tampon or tampon proposed by the invention is that it strengthens the pelvic floor.

To provide a clearer understanding, the invention will be described in more detail below with reference to examples of embodiments illustrated in the appended drawings.

These are highly schematic, simplified diagrams illustrating the following.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described. Individual features or combinations of features from the different embodiments illustrated and described may be construed as independent inventive solutions or solutions proposed by the invention in their own right.

All the figures relating to ranges of values in the description should be construed as meaning that they include any and all part-ranges, in which case, for example, the range of 1 to 10 should be understood as including all part-ranges starting from the lower limit of 1 to the upper limit of 10, i.e. all part-ranges starting with a lower limit of 1 or more and ending with an upper limit of 10 or less, e.g. 1 to 1.7, or 3.2 to 8.1 or 5.5 to 10. A value within a specified range of values may remain constant across a length of the tampon or may vary within these limits. Maximum values and minimum values should be understood as meaning that the bottom and top threshold values are defined by the physical and technical feasible possibilities and figures given for length or diameter greater and less than "zero" are "infinite".

The embodiments illustrated as examples represent possible variants of the everyday tampon or tampon proposed by the invention, and it should be pointed out at this stage that the invention is not specifically limited to the variants specifically illustrated, and instead the individual variants may be used in different combinations with one another and these possible variations lie within the reach of the person skilled in this technical field given the disclosed technical teaching. Accordingly, all conceivable variants which can be obtained by combining individual details of the variants described and illustrated are possible and fall within the scope of the invention.

For the sake of good order, finally, it should be pointed out that, in order to provide a clearer understanding of the structure of the tampon, it and its constituent parts are illustrated to a certain extent out of scale and/or on an enlarged scale and/or on a reduced scale.

The objective underlying the independent inventive solutions may be found in the description.

Figure 1:
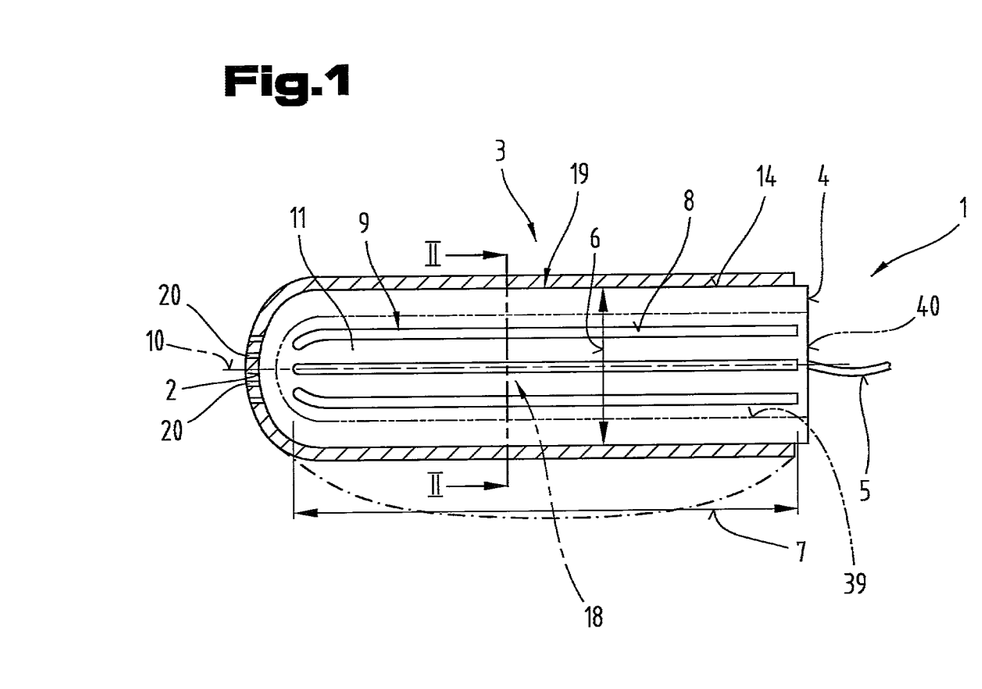
FIG. 1 a side view of a tampon proposed by the invention with recesses.
Figure 2:
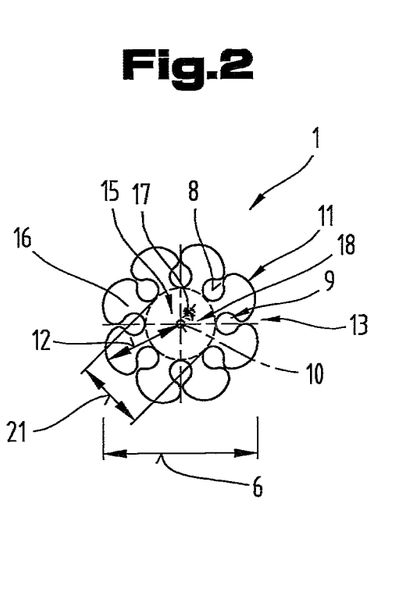
FIG. 2 an end-on view of the tampon in section along line II-II indicated in FIG. 1.

FIGS. 1 and 2 illustrate a tampon 1 for days between menstruation having a dome-shaped proximal end 2, an elongate, cylindrical middle part 3, a distal end 4 and an extraction means 5 extending out from the latter, in particular a cord. The cylindrical or frustoconical middle part 3 extends with an essentially constant or widening or varying diameter 6 to its proximal end 2. Recesses 9 formed by grooves 8, for example, are provided at least across a part of its length 7 in the tampon or in the middle part 3. An external diameter 6 of the absorbent body 16 or a bounding volume 37 surrounding the absorbent body 16 may have a value of between 2 mm and 14 mm, or 6 to 10 mm or less than 8 mm. The bounding volume 37 is a fictitious external surface inside which the external circumference of the tampon 1 or absorbent body 16 lies at least partially in contact or at a tangent.

The maximum value of the diameter 6 may be a value between the specified value limits or below the value limit and this maximum value across the entire length 7 of the tampon 1 or at least across a part-region may be constant or may optionally be variable across the length 7 of the tampon 1 or a part thereof may be variable within the specified value limits or below a maximum value of the diameter 6, i.e. varies.

As schematically illustrated in FIG. 1, the tampon 1 may have a circumferentially extending recess 38 in the middle part 3—see dotted-dashed line—for example a groove or a recess with any three-dimensional shape.

At least a part of the middle part 3 of the absorbent body 16 or a bounding volume 37 containing it or the tampon 1 may be cylindrical in shape. However, it would also be possible for at least the middle part 3 of the absorbent body 16 or tampon 1 or a bounding volume 37 containing it to be conical or frustoconical.

The cylinder or cone or truncated cone may also extend continuously from the proximal end 2 to the distal end 4.

In the case of all the geometric shapes of the absorbent body 16 listed above, any cross-sectional changes across the length extending towards the longitudinal mid-axis 10 are possible, e.g. a wave-shaped contour or recesses extending at least around a part of the circumference or extending in the longitudinal direction and disposed inside the bounding volume 37.

The expression "distal end" 4 in the context used here refers to that portion of the arrangement and its parts which are farthest away from a user's body when the tampon 1 is introduced into a body opening, e.g. the vagina. The expression "proximal end" 2 relates to those portions of the arrangement and their parts which are closest to a user's body when the tampon is or has been introduced. Accordingly, the expressions "proximal" or "distal" as used here mean that a specific part or a specific structure of the arrangement or its parts is closer to the proximal end 2 or to the distal end 4 of the arrangement or its parts. Similarly, the expressions "proximal direction" or "distal direction" refer to the directions towards the proximal end 2 or towards the distal end 4 of the tampon 1.

The tampon 1 or at least its middle part 3 may have a substantially cylindrical shape or cylindrical bounding surface. Another option is for the middle part to be tapered from the middle part 3 in the distal and/or proximal direction. This taper may be conical or of any other geometric shape. Especially in the proximal direction, the middle part 3 may also become wider.

The recesses 9 on the external face or in the surface of the tampon 1 may be formed by regions disposed directly adjacent to one another or merging with one another disposed at a different distance from the central longitudinal mid-axis 10 of the tampon 1, and the regions 11 disposed at the farthest distance 12 from the longitudinal mid-axis 10 have ribs whilst the regions 13 lying in between have grooves.

In the region 13 of the recess 9, the density of the material from which an absorbent body of the tampon 1 is made may correspond to the density in region 11, which corresponds to the recess 9 of adjacent raised areas. However, it would also be possible for the density in the region 13 of the recesses 9 or in the region 11 of the raised areas to be higher. The external face or surface 14 of the tampon 1 may also be of a substantially smooth design.

The external face or surface 14 is formed by both the partial surface constituting the regions 13 having a radial recess 9, e.g. the grooves 8, and the partial surfaces constituting the regions 11 adjoining these regions 13.

A groove 8 constitutes a clear region of a radial recess 9 on the external face of the tampon 1, which can be at least partially defined by its length, width, depth and orientation. The length of a groove 8 is usually greater than its depth.

Each of the recesses 9 and grooves 8 may extend continuously across at least a part-length of the length 7 or may be interrupted.

The tampon 1 or its middle part 3 may have between 2 and 3 recesses 9 or grooves 8, for example. By way of example, tampons 1 may have 2, 3, 4, 5, 6, 7, 8, 9, 10, 11 or 12 grooves. The tampon 1 may have an even or odd number of recesses 9 and grooves 8. Due to manufacturing requirements, an even number may be preferable.

Based on another example of an embodiment, the recesses 9 and grooves 8 extending in the direction of the longitudinal mid-axis 10 of the everyday tampon 1 may form a spiral or helical pattern in the axial direction. These spiral-shaped or helically shaped recesses 9 and grooves 8 are longer than grooves extending parallel with the longitudinal mid-axis 10 of the tampon 1. These recesses 9 and grooves 8 cover a bigger region the surface 14 or external face 7. Based on the number of recesses 9 and grooves 8 and their length and depth, the total surface 14 used to absorb liquid can be adapted to the required absorption capacity. In particular, this also means that by directing liquids into a central region 15 of the absorbent body 16 of the tampons 1, it is possible to adapt to different requirements.

In this connection, once the recesses 9, in particular the grooves 8, have been embossed into the absorbent body 16 of the tampon 1, it is also of advantage to deform or compress the regions 11 left in between, for example, so as to obtain a mushroom-shaped cross-section, as may be seen more clearly from FIG. 2. As a result, liquids are also absorbed and adhere to the schematically indicated fibers and filaments 17 in a core region 18 formed between the recesses 9 as well as in the regions 11 having an approximately mushroom-shaped cross-section. This is of advantage in the case of this particular tampon 1 because a slimmer volume of the absorbent body 16 enables a correspondingly rapid and high absorption of moisture, especially on days between menstruation times.

The maximum external diameter 6 of the tampon 1 or its middle part 3 may be substantially constant or may vary in the longitudinal direction. The part of the tampon 1 close to the distal extraction end may have a bigger maximum external diameter 6 than the remaining part of the middle part 3. This extra thickness at the bottom end of the tampon 1 reduces the risk of body fluid leaking when the tampon 1 is positioned in the vagina.

In one example of an embodiment, the density of the absorbent material may be substantially constant across the cross-section of the tampon 1.

In another example of an embodiment, the central region 15 of the tampon 1 or absorbent body 16 may be made from highly compressed, absorbent fibrous material.

Furthermore, it is also possible to provide a very highly compressed central region 15, whereas the regions 13 lying between the recesses 9 and grooves 8 are less compressed so that they have a higher intrinsic, elastic rebound capacity. This lower density and higher elasticity in these regions lying between the recesses 9 and grooves 8 enable the pressure acting on the body parts in contact with the tampon 1 to be reduced and also result in greater comfort with a more pleasant sensation for the user because the movements of the body parts in contact with the absorbent body 16 are better able to conform to the shape of the ribs or regions 11 formed between the recesses 9 and grooves 8.

This tampon 1 has a narrowed proximal insertion end 2, i.e. an insertion end with a smaller diameter in cross-section than the diameter 6 of the middle part 3 of the tampon 1. The insertion end may be conical or rounded, for example, and may preferably be of a rounded dome shape. Due to the design of the proximal end 2, the tampon 1 can also be inserted deeper into the vagina, i.e. closer to the neck of the uterus, which is advantageously conducive to moistening the tampon 1 because the liquid to be absorbed is deep in the vagina. Tampons 1 with a narrowed insertion end, in particular a rounded or round dome-shaped proximal end 2, are therefore generally preferred by consumers.

The absorbent fibrous material used for the tampon 1 and its absorbent body 16 may be any absorbent material 36 with a good absorption capacity and modulus of elasticity which can absorb and/or retain liquid. The absorbent structure may be made in a plurality of sizes and shapes and from a plurality of liquid-absorbing materials 36.

Naturally, it is desirable to use absorbent materials 36 with a minimum content of soluble foreign materials because the product remains in the body for a certain amount of time. Retained soluble foreign materials could pose a safety risk if toxic or irritant.

A list of materials which may be used includes materials containing cellulose, such as, for example, rayon, cotton, cellulose, cellulose wadding, layered tissue materials, sphagnum, bamboo and chemically reinforced, modified or cross-linked cellulose fibers; synthetic materials such as, for example, polyester fibers, polyolefin fibers, absorbent foams, for example an elastically resilient polyurethane foam, absorbent sponges, extremely absorbent polymers, absorbent gel-forming materials, processed fibers such as capillary channel fibers and fibers with several members, for example; synthetic fibers or an equivalent material or combinations of materials or mixtures thereof.

If using such synthetic foams, it is also possible to partially close the outer skin, for example by setting a specific temperature during the process of manufacturing the absorbent body, i.e. produce a closed skin in the external region due to a partial temperature effect. This makes it more difficult for liquid absorbed in the foam structure to escape or prevents it altogether. It may be of advantage to opt for this design for the distal end region 4 of the tampon 1 in particular.

Within the context of the invention, the tampon 1 may be made from a broad range of materials which retain their state for a long time under the conditions prevailing in the region of the vagina and uterus, i.e. at body temperature and a pH value of ca. 4, and do not give off toxic substances or solutions damaging to the mucous membranes or similar. Advantages may be gained above all by using flexible polyurethane foams with a very low volumetric weight and a predominantly open-celled structure. Using a more absorbent material further reduces the risk of liquid leaking.

Another advantage of such foamed structures is that the open cells in the supplied state or before being introduced into the vagina can be filled with medicaments or lubricant which can be discharged to the mucous membranes of the vagina and uterus when inserted.

Based on one embodiment, the surface of the tampon 1 may be at least partially provided with an at least partially liquid-permeable casing 19. The casing 19 provides a smoother surface. This reduces the risk of fibers becoming detached from the surface 14 of the tampon 1 during use. The likelihood of the tampon material being lost is also reduced. The casing 19 does not usually reduce the absorption ability and absorption capacity or the ability of the tampon 1 to expand. The use of casings on tampons is well known in this technical field, as are the materials suitable for these casings. The casing 19 may be dispensed with at the proximal insertion end 2 or front end of the tampon 1 so that the body fluid can be more effectively absorbed there, or it may be provided with perforations or openings 20, for example, at least in this region.

It is also of advantage if the materials used are biologically degradable and are made from PLA, for example, or other such biologically degradable synthetic materials or synthetic mixtures or filaments or fibers, or recycled plastics, such as R-PP, R-PET or such like, optionally in different mixtures or as multi-layered parts made from these materials 36.

As far as the tampon 1 is concerned, given that it is often intended for use between menstruation phases or times or even for daily use, it is of advantage if the mucous membranes in the region of the vagina, as well as the circularly extending muscles, are placed under as little stress as possible. Accordingly, the features that are of particular advantage are those whereby pressure on the mucous membranes is low, including when the vagina is in the relaxed state, thereby reducing or even totally preventing erosion of the mucous membrane and/or damage and/or detrimental change to the pH value in the region of the mucous membranes.

To this end, it has proved to be of advantage to make the length 7 of the everyday tampon 1 and/or its diameter 6 and/or its volume and/or its weight within a specific ratio.

For example, it is of advantage if a diameter 6 of the tampon 1 has a value of between 6 and 14 mm, preferably less than 10 mm, for example preferably less than 8 mm.

The specific choice of value for the diameter 6 of the tampon 1 offers an easy way of adapting to different anatomical requirements for different persons. In addition, the size of the diameter 6 can be used to determine the volume of absorbent material and hence the amount of liquid absorbed, so that for different conditions and different persons, tampons 1 with different moisture absorption levels can be produced and adapted to the requirements of different persons. Accordingly, if a higher capacity to absorb liquid is required, the absorbent body 16 can be made from an absorbent material 36 throughout its entire volume. If tampons 1 with a lower absorption capacity are being produced, it is also possible to make a central part 15 or a core region 18 from either fibrous material or another moisture-absorbing material, for example. If fibrous materials 36 are provided in the core region 18 or central region 15, it is also possible for it to absorb a lower liquid quantity for the same volume than the material 36 of the absorbent body 16 surrounding these central or core regions 15, 18.

Using a central or core region 15, 18 of this type also enables the quantity of absorbent material 36 used for the absorbent body 16 to be varied and adapted so that if a larger external diameter 6 of the tampon 1 is needed for anatomical reasons but it needs to have a lower capacity to absorb liquids, a material can be used in the central or core region 15, 18 which has an extremely low or absolutely no moisture-absorbing capacity.

In the case of these embodiments, it is also to be recommended that the extraction means 5 is connected to either the absorbent body 16 and/or to the central or core region 15, 18 of the tampon. This also ensures that the tampon can be reliably extracted if the outer casing 19 of the absorbent body 16 surrounding the central or core region 15, 18 is made from only lightly compressed fibers or from a thin layer with a low tearing resistance.

The length 7 of a tampon 1 is advantageously shorter than 40 mm and it preferably has a minimum diameter 6 of 5 mm. A practical diameter 6 for a tampon 1 of the type used on days between menstruation times is a length 7 of between 30 and 38 mm but for specific applications it is also possible for the length 7 to be between 30 mm and 10 mm. This means that the length 7 may be of any value between 10 and 30 mm. The same also applies to the length values specified above.

In terms of the dimensions specified for this tampon 1 above, it is of advantage if the basis weight of the strip used to produce the tampon 1 relative to a width which preferably approximately corresponds to the length of the tampon 1 is selected so as to be between a minimum value of 1 g/lfm and 30 g/lfm. As a result, a weight of the tampon 1 without the extraction means 5 will be less than 2 g, preferably less than 1.7 g, but for example also between 1.5 and 0.5 g.

In the case of the digital tampon 1 mentioned above which usually has a compressed core region 18 of the absorbent body 16, it is recommended that a diameter 21 for the more highly compressed core region 15 of the absorbent body 16 be based on values of less than 6 mm, preferably less than 4 mm down to a lower value of 0.5 mm.

As a result, in the regions of the absorbent body 16 extending around the circumference of the central or core region 15, 18, there is a less compressed fibrous material which has a stronger suction effect and better capillary action to which the liquid droplets are better able to adhere.

It may also be of advantage for the tampon 1, in particular its absorbent body 16, to have a higher elasticity to permit deformations about axes extending perpendicular to the longitudinal mid-axis 10, thereby enabling it to adapt more readily to the conditions in the interior of the user's body.

Advantageously adapting the elasticity of the absorbent body 16 in the direction extending radially with respect to its longitudinal axis 10 makes it possible to adapt to different sensitivities of the user because the induced pressing effects on the body parts can be made variable. This makes it easy to deal with the problem of pressure, irritation to the mucous membranes and adapt to the circumstances of different persons so that different tampons 1 can be produced to meet different requirements.

Furthermore, this also enables the weight of the absorbent body 16 without the extraction means 5 to be reduced accordingly, which means that pressure on the user's body parts lying in contact with the absorbent body can also be reduced accordingly, and this is the case both in the dry state and in the moist state after having absorbed liquid or moisture. At the same time, downwardly directed forces on the sphincter muscle of the bladder in the region of the bladder outlet can likewise be reduced.

Especially in the case of tampons 1 for which the liquid to be absorbed is based on smaller quantities per unit of time, a less compressed structure in a larger cross-sectional region of the absorbent body 16 offers an advantage.

Depending on the material 36 used for the absorbent body 16, for example by using rayon fibers or fibers and filaments of cellulose, for example using a structure type of the crystal modification of cellulose II, this absorption quantity of the absorbent body 16 can be further increased and the volume can therefore be kept smaller, advantageously enabling an absorption capacity of the absorbent body 16 to be achieved that is less than 4 ml.

However, the absorption capacity of the absorbent body 16 can be kept at very low values, as mentioned above, by providing regions with an extremely low moisture absorption capacity or even a moisture-repelling material in the central or core region 15, 18. This represents an easy way of varying the quantity of liquid absorbed by the respective absorbent body 16. An advantageous absorption quantity of liquid has proved to be 4 ml or less than 4 ml. However, given that the liquids discharged by different persons on different days may also vary, it is also of advantage to produce this type of tampon 1 with a liquid-absorption quantity of 3 to 3.5 ml or of only 2 ml.

The figures given for these values for the liquid quantity in ml and for the weight in g should be taken as essentially equivalent.

The tampon 1 usually has an extraction means 5 such as a retraction cord extending out from the proximal extraction end of the tampon 1 and secured in the absorbent body 16 of the tampon 1 to make it easier to pull out the tampon 1 after use. The extraction means 5 may preferably be elastic and water-repellant and must have enough tension to ensure that it does not tear off when taking out the tampon 1. It may be made from any material used for a retraction cord in the prior art. It may be an individual cord, a strip or a plurality of strings. A water-repellant cotton thread, a water-repellant polyester thread or a mixture thereof have proved to be effective materials for the extraction means 5 or retraction cord. With polyester, the extraction means 5 can be made stronger. The extraction means 5 can be secured in the tampon 1 by any means known to the person skilled in the art. As mentioned above, the extraction means 5 or retraction cord may be stitched to the strip part from which the absorbent body 16 of the tampon 1 is made or to the two strip parts forming the absorbent body 16, through which the extraction means 5 extends from at least two mutually spaced apart points disposed within a loop of this extraction means 5. However, the extraction means 5 may also form a loop, extending through the strip part of the absorbent body 16. Other options are to weave in, weld or glue the extraction means 5 to the absorbent body 16 or strip parts from which it is made.

Another option is to position the material in the interior of a tampon 1 or absorbent body 16 and as soon as the latter becomes moist, the material is released. This would correspond to a delayed release.

Figure 3:
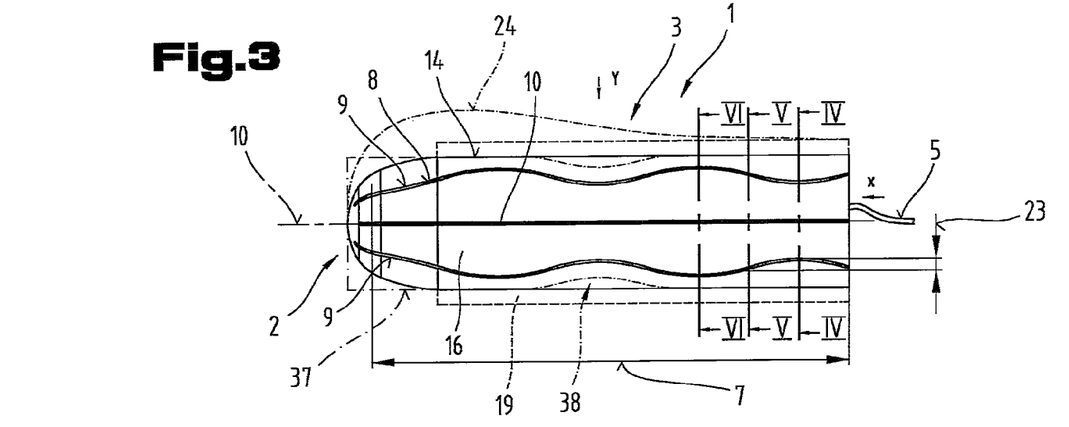
FIG. 3 another embodiment of the tampon with a conically tapering distal end and with wave-shaped recesses extending in the longitudinal direction of the tampon body, such as grooves or flutes, for example.
Figure 4:
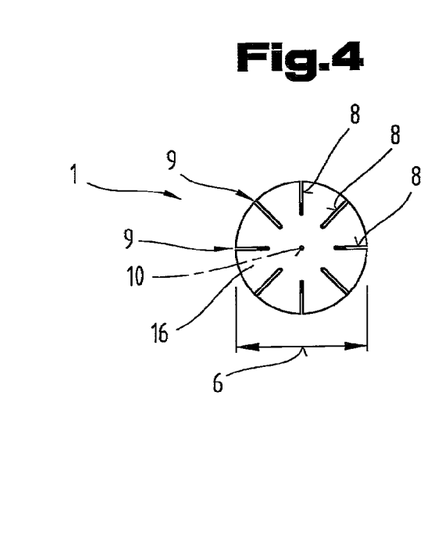
FIG. 4 an end-on view of the tampon body from FIG. 3 in section along line IV-IV.
Figure 5:
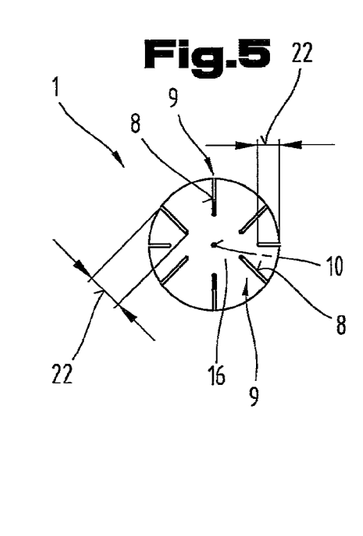
FIG. 5 end-on views of the tampon body from FIG. 3 in section along line V-V.
Figure 6:
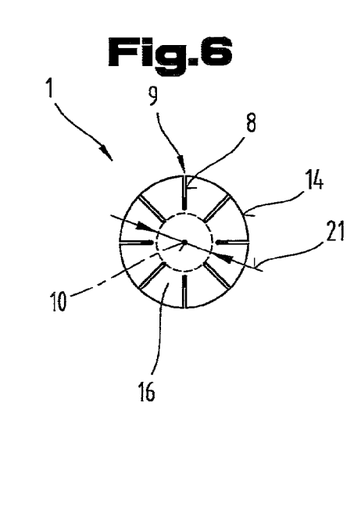
FIG. 6 end-on views of the tampon body from FIG. 3 in section along line VI-VI.

Another embodiment of a tampon 1 is illustrated in FIGS. 3 to 6. It has an elongate absorbent body 16 with a conically tapering and dome-shaped proximal end 2 extending across a part of its length 7. Recesses 9, for example grooves 8, are provided along the length 7 of the tampon 1 on the external face or in the surface 14, for example grooves 8. These recesses 9, in particular grooves 8, may have a wave-shaped contour relative to the longitudinal mid-axis 10, both in the circumferential direction of the absorbent body 16 and in the depth 22, as schematically illustrated in the drawings in the end-on views in different regions in the longitudinal direction spaced apart from the longitudinal mid-axis 10, as illustrated in FIGS. 4 to 6. A height 23 of the amplitude of this wave-shaped contour may extend uniformly across the length 7 of the absorbent body 16 or alternatively may assume different values along the length 7.

The same applies to the wave-shaped contour of the depth 22, where the height of the amplitude for the wave-shaped contour of the recesses 9 or grooves 8 may likewise extend uniformly across the length 7 of the absorbent body 16 or a part thereof or may vary in size in different regions, for example in the middle part 3 or in the region of the ends 2, 4.

In the case of many tampons that are used as digital tampons, in other words that are inserted in the vagina manually by the user, it is recommendable for the central or core region 15, 18, which may have a diameter 21, to be compressed to a greater degree so that it can assume a rod-shaped supporting function for the tampon 1.

If the tampon 1 based on this embodiment is not provided with a full casing 19, made from a nonwoven for example, this casing 19 extends across only a part of the length 7 of the tampon 1, as schematically indicated by broken lines in FIG. 3, and the absorbent body 16 will swell from the proximal end 2 in the radial direction on becoming wet and will assume a geometric shape such as indicated by the dotted-dashed line 24, although this is highly schematic and over-exaggerated. If the casing 19 provided over the illustrated part-region of the length 7 of the tampon 1 is provided around only the length of the middle part 3, the swelling in the radial direction will be less pronounced in the middle region than if the casing 19 were not provided at all.

Figure 7:
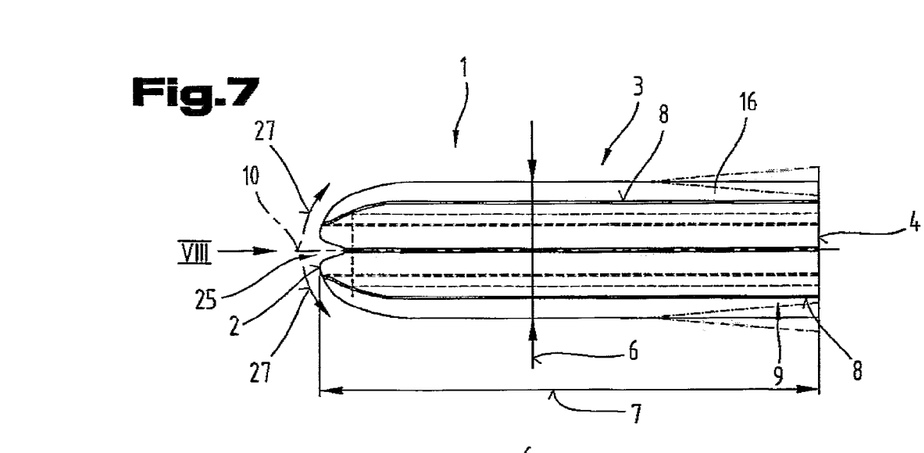
FIG. 7 an embodiment of the tampon proposed by the invention with recesses extending parallel with the longitudinal axis of the tampon body and a recess in the region of the distal end of the tampon.
Figure 8:
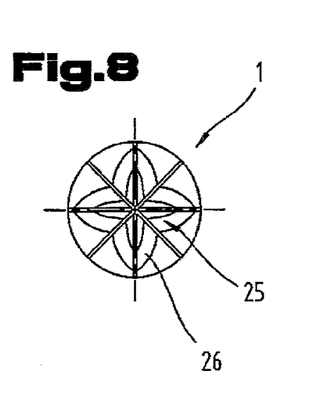
FIG. 8 an end-on view of the tampon body from FIG. 7 in the direction of arrow VIII indicated in FIG. 7.

Another embodiment of a tampon 1 proposed by the invention is illustrated in FIGS. 7 and 8. This tampon 1 or its absorbent body 16 has recesses 9 and longitudinal grooves 8 extending in the direction of the longitudinal mid-axis 10. The middle part 3 of the absorbent body 16 is adjoined by an end region tapering conically in the direction of the proximal end 2 having a cylindrical diameter, although it would also be possible to provide a diameter 6 in the region of the distal end 4, as indicated by dotted-dashed lines, that is smaller or bigger than in the middle part 3.

The contour of the recesses 9 need not necessarily extend in a straight line and parallel with the longitudinal mid-axis 10 and instead, as illustrated in FIG. 3 for example, the contour may be wave-shaped both in the circumferential direction of the absorbent body 16 and in the direction of the depth 22. Amongst other things, it would also be possible for the recesses to extend helically in the manner of a screw thread, for example, at least across a part of the length of the middle part 3.

Furthermore, in the region of the distal end 2, the absorbent body 16 may be provided with a recess 25.

The protruding leaf-shaped end regions 26 of the absorbent body may also be shaped so that when exposed to moisture, they open outwards for example, in the direction of arrows 27, in a manner similar to the flower petals of a tulip, thereby creating an additional catchment zone or catchment area in which liquid from inside the body can collect before being absorbed in the individual recesses 9 and grooves 8 distributed around the length 7 of the absorbent body 16.

Figure 9:
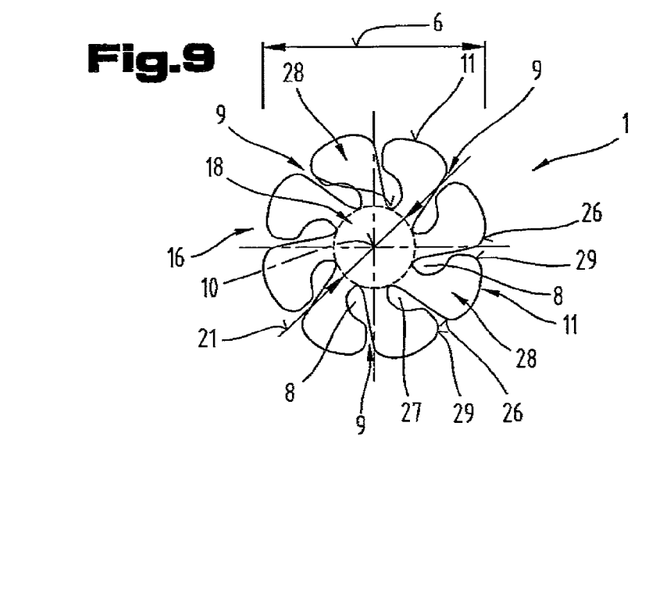
FIG. 9 an end-on view of another embodiment of the tampon body in section with ribs forming a special design of the outer surface of the tampon body.
Figure 10:
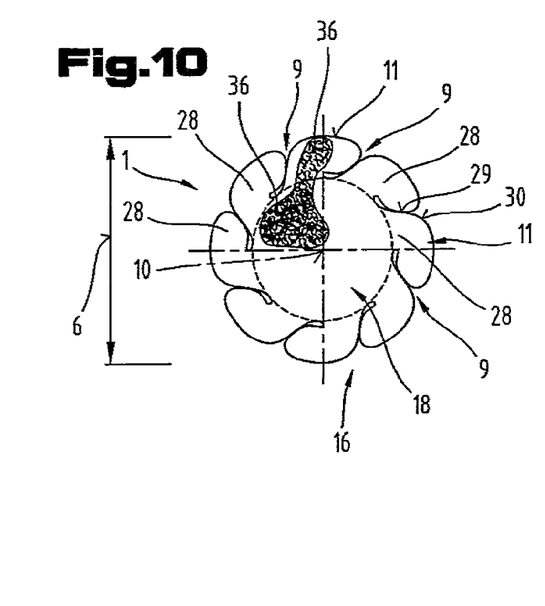
FIG. 10 an end-on view of another embodiment of the tampon body in section with ribs forming a special design of the outer surface of the tampon body.

FIGS. 9 and 10 also illustrate different designs of the cross-sectional shape of the rib-type regions 11 adjacent to the recesses 9. The ribs 28 have an L-shaped or shoe-shaped cross-section in the plan view illustrated in FIG. 9. The front ends 29 of the regions 11 lie almost against the rear end regions 30, thereby creating a cavity 31 between them or surrounded by them, which extends at least across a part of the length 7 of the absorbent body 16. This creates a large surface 14 of the absorbent body 16 to absorb moisture or liquid and also ensures that moisture or liquid is directed to the regions of the absorbent body 16 farther away from the distal end 2 where it can be absorbed by them, thereby making optimum use of the absorption capacity of the tampon 1.

In the embodiment illustrated in FIG. 10, the ribs 28 which extend more or less radially outwards during the process of producing the recesses 9 are bent over in the radial direction and re-shaped so that they form a circumferentially extending, outer bounding surface of the tampon 1. The end regions 29 of the ribs 28 therefore lie directly against the end regions 30 of the adjacent rib 28. As a result of this radial re-shaping, the recess 8 forms a longer capillary-type channel, which produces a stronger suction effect into the interior of the absorbent body 16.

Figure 11:
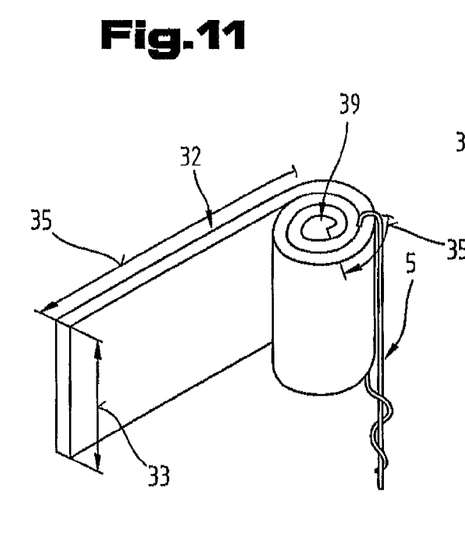
FIG. 11 a simplified schematic diagram illustrating a strip part of a strip for producing a tampon body for a tampon.
Figure 12:
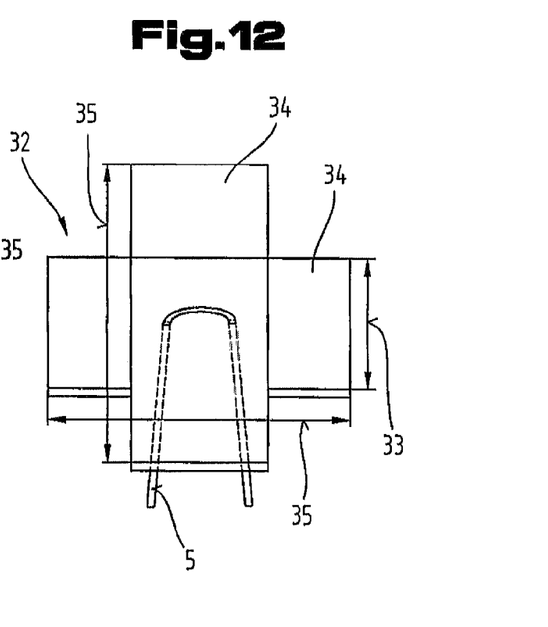
FIG. 12 a simplified schematic diagram illustrating the disposition of strip parts of a strip for producing a mushroom-shaped tampon based on the invention.

FIG. 11 illustrates the prefabricated winding used to make the absorbent body 16 during production of the tampon 1 in the semi-finished state. Windings of this type are primarily used for so-called digital tampons. They consist of a strip 32 with a width 33 of 20 to 50 mm, preferably less than 38 mm, e.g. 15 to 30 mm. Strip parts 34 are cut to length from this strip as shown in FIG. 12, with an unwound extended length 35 which is determined depending on a desired volume of the absorbent body 16 or intended diameter 6 and/or the linear meter weight of the strip 32 of the tampon 1. The actual tampon may have a length of ca. 250 mm or shorter, e.g. between 80 and 150 mm, preferably between 100 and 120 mm.

The linear meter weight of such a strip with a width 33 of the cutting of the strip part 34 for producing a tampon of a corresponding width is only between 1 and 30 g. The tampons in the form of digital tampons are manufactured in such a way that the lengthways strip part 34 is rolled about an axis extending transversely to the longitudinal direction of the strip 32 to obtain a cylindrical body. The cylindrical body is then compressed in the radial direction and subjected to a shaping process so that a cone-shaped, tapering rounded end is obtained, namely at the distal end 2, or a spherical or dome-shaped end region, as illustrated in FIGS. 1 to 10, for example. The oppositely lying end from which the extraction means 5, for example the retraction cord, protruded prior to rolling the strip and extended out from the width side of the strip, has a flat termination or concavely cambered end face.

As standard practice when producing digital tampons, as illustrated in FIGS. 1 to 10, individual lengthways regions of the cylindrical blank are compressed to a greater degree to create a stiffer central or core region 15, 18 and the tampon regions left protruding out between these pressed grooves are compressed to a lesser degree and therefore have a higher elasticity.

To produce these tampons, as already described above in connection with different types of tampons, any materials 36 known from the prior art may be used and, as schematically indicated in FIG. 10, the fibers or filaments or cells formed may be compressed to a greater or lesser degree.

Instead of subjecting individual parts of the cylindrical blank of the absorbent body 16 to a higher degree of compression, the central or core region 15, 18 may also be formed by inserting a molded body, as indicated in FIG. 1 by two dotted-dashed lines, for example. This inserted molded body may be made from a moisture-repellant material, although it would also be possible to use a fibrous material 36 which is processed accordingly, e.g. by compression or by using the corresponding materials, so that it holds a lower quantity of liquid per unit by volume than the same unit of volume of the material 36 used for the absorbent body 16. It is also possible for the blank to be made from a liquid-repellant material, for example in the form of a plastic part.

This blank or the central or core region 15,18 formed by it is then enclosed in the absorbent body 26, at least in the region of its proximal end 2 and in the region of the middle part 3, and the absorbent body is preferably formed by a cylindrical hollow body, which may be closed in the region forming the proximal end and open or provided with an opening at the oppositely lying distal end 4 of the tampon 1 so that a blank forming the central or core region 15,18 can be introduced into this casing forming a finger.

Based on the volume of the central or core region 15, 18 which absorbs a lesser amount of or virtually no moisture, the quantity of liquid which can be absorbed by this absorbent body 16 can be easily adapted to different applications regardless of the overall diameter of the tampon 1. This offers a high degree of flexibility in terms of both the quantity of liquid which can be absorbed by the tampon 1 on the one hand, and does so irrespective of the different diameters of the central or core region 15, 18—which may be of various three-dimensional shapes—needed to cater for different persons for anatomical reasons. During the process of manufacturing the absorbent body 16 with a radial elastic pre-tensioning, the latter can be pulled over the blank forming the central or core region 15, 18 and adapted to its external shape, thereby enabling the tampon 1 proposed by the invention to be made in a wide variety of external shapes.

The absorbent body 16 therefore has a cavity 39 which is accessible from an opening 40 in the absorbent body 16 at the end facing the distal end region 4 or the oppositely lying end region forming the proximal end 2.

It is also possible for the individual tampons 1 to be provided with a nonwoven cover or with some other cover of a net-type material or with perforations, which prevents any loss of fibers and which in particular is intended to reduce or prevent increased friction between the mucous membranes of the vagina and the outer surface of the tampon and prevent fiber loss.

Figure 13:
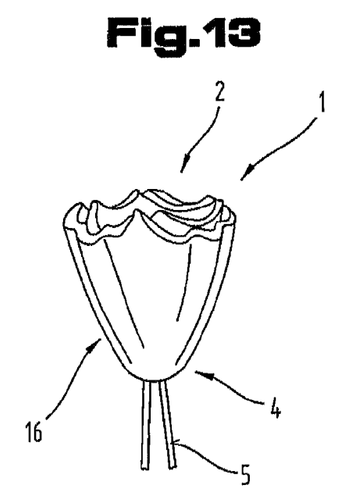
FIG. 13 a simplified schematic diagram illustrating the strip parts for the absorbent body of the tampon proposed by the invention in an intermediate position shaped in a tulip arrangement.
Figure 14:
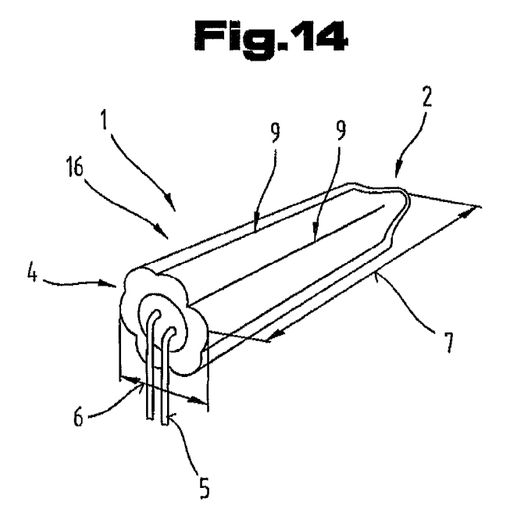
FIG. 14 a simplified schematic diagram illustrating the absorbent body of a tampon proposed by the invention in the finished state.

FIGS. 12 to 14 illustrate a different type of tampon 1, based on a manufacturing process that is different from the manufacturing process described above. This embodiment of the tampon 1 is a so-called mushroom head tampon, for which two approximately rectangular strip parts 34 with a length 35 of between 40 and 80 mm and a width 33 of 10 to 30 mm are laid one on top of the other with their longitudinal mid-axes respectively offset by 90°. In the region adjacent to the intersection points, lying one on top of the other, of the diagonals of the two strip parts 35 indicated by dotted-dashed lines, a loop of an extraction mean 5 is pulled through the two strip parts 35. The free ends of the two strip parts 35 are then folded together in an arrangement akin to a tulip flower—see FIG. 13—to create a substantially cylindrical body, with the extraction means 5 extending out from the end region, which is of a mushroom shape or spherical dome shape or of a conical design. The cylindrical blank prefabricated in this manner is usually compressed at a raised temperature by means of pressing dies acting radially on it so that it ultimately assumes a cylindrical shape, as illustrated in FIG. 14. The material used for this strip 32 may be any soft absorbent material, such as cotton, gauze or a multi-layered material with a high absorption capacity. The linear meter weight for a width approximately corresponding to the length 35 of the strip part 34 is usually between 10 and 35 g.

Figure 15:
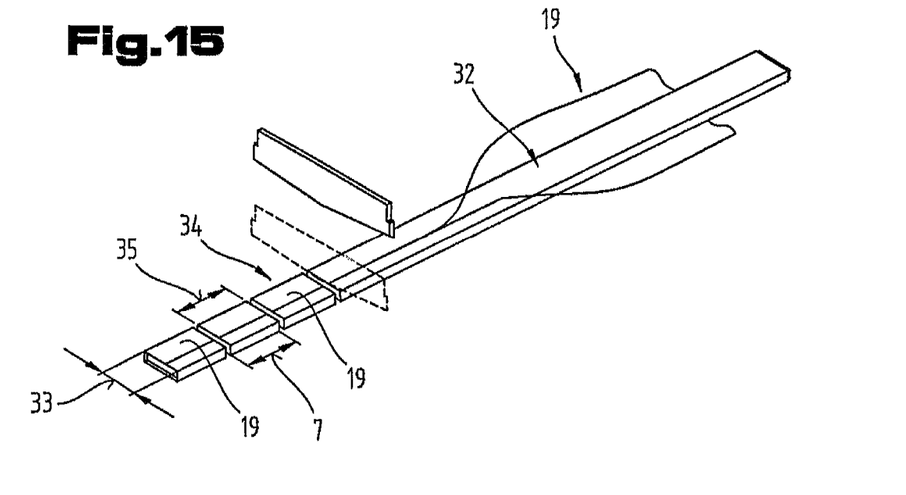
FIG. 15 a schematic diagram illustrating a strip for producing a tampon proposed by the invention with the strip parts thereof separated.
Figure 16:
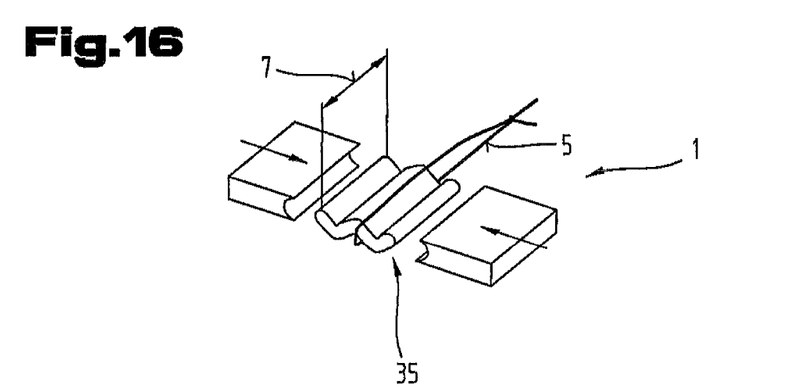
FIG. 16 a simplified schematic diagram illustrating the pre-formed strip part from FIG. 15 with the extraction means attached to it and the dies for shaping the strip part.
Figure 17:
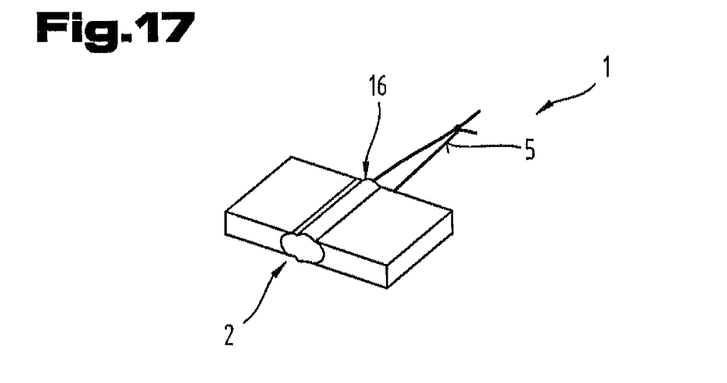
FIG. 17 a simplified diagram illustrating a finished, shaped tampon proposed by the invention made from a prefabricated strip part illustrated in FIG. 16.

Another possible embodiment for the tampon 1 is illustrated in FIGS. 15 to 17. This special shape of the tampon 1 falls within the category known as the "tea bag tampon" and comprises a rectangular cutting from a strip of an absorbent material, such as cotton, gauze, wadding or similar.

During the course of the production process, as schematically illustrated in FIG. 15, this strip 32 is wound with a material layer, for example a nonwoven, to produce a casing 19. The strip 32 wound with the casing 19 is cut by means of a schematically indicated blade into strip parts 34. These strip parts 34 usually have a length of 20 to 50 mm, preferably 40 mm, in the longitudinal direction of the strip 32 and a width of 40 mm or 20 to 40 mm. An extraction means 5, for example a retraction cord, is stitched or glued to this strip part 34 in the direction of the longitudinal mid-axis. It extends out beyond one of the two lengthways ends of the strip parts 34 in the longitudinal direction, as illustrated in FIG. 16.

The linear meter weight of the strip 32 used to produce the tampon 1 for a width 33 of the strip 32 is a linear meter weight of between 10 and 40 g, preferably between 10 and 25 g.

This strip part 34 is then folded in a zig-zag shape or W-shape by means of two pressing punches displaceable in the direction of the arrows, as illustrated in FIG. 16 and shaped to an approximately cylindrical shape, as illustrated in FIG. 17. In this shaped and compressed form, the absorbent body 16 produced from the strip part 34 is usually inserted in a tubular applicator for insertion into the vagina.

Such so-called tea bag tampons (tampons with a stitched cord) are usually only inserted in the vagina by means of applicators.

All figures given in connection with absorption capacity and the absorption capacity of the absorbent body 16 and the liquid quantities which can be absorbed by tampons 1 proposed by the invention are based on the standard test of EDANA (European Disposables and Nonwoven Association), using the Syngina method.

The relevant EDANA regulation is entitled "Tampon absorbency" under reference number 350.0-02 in the English version of February 2002.

This type of tampon can therefore also be produced as a tampon 1 and the tampon 1 can be mechanically inserted in the vagina in what is the usual way for the user by means of an applicator with a smaller diameter.

The tampon 1 may be made both as a "digital tampon" which is inserted in the vagina by the user manually with the finger and as a tampon for use with applicators.

The invention claimed is:

1. A tampon for days between menstruation, the tampon comprising
    an absorbent body having a middle part, a proximal end, and a distal end, and
    an extractor connected to the absorbent body,
    wherein the absorbent body has a volume and is made from an absorbent material throughout the entire volume,
    wherein the tampon is designed for the days between menstruation times and the absorbent material has a volume to absorb a liquid quantity of between 0.5 g and 4 g, and
    wherein the absorbent body has a length of between 38 and 30 mm and a diameter of the absorbent body or a bounding volume surrounding the absorbent body is at most 10 mm.

2. The tampon according to claim 1, wherein the absorbent material is made from fibrous material.

3. The tampon according to claim 1, wherein the absorbent material is made from a compressed, fibrous material.

4. The tampon according to claim 1, wherein the volume of the absorbent material of the absorbent body is designed to absorb a liquid quantity of between 0.5 g and 3.5 g.

5. The tampon according to claim 1, wherein a diameter of the absorbent body or a bounding volume surrounding the absorbent body has a value between 2 and 10 mm.

6. The tampon according to claim 1, wherein at least the middle part of the absorbent body or a middle part of a bounding volume surrounding the absorbent body is cylindrical in shape.

7. The tampon according to claim 1, wherein the absorbent material comprises a first absorbent material and a second absorbent material, wherein the second absorbent material is a fibrous material and is disposed in a core region at least inside the middle part of the absorbent body, and
    wherein the second absorbent material is designed to absorb a smaller liquid quantity than the first absorbent material absorbs for the same volume.

8. The tampon according to claim 1, further comprising a moisture-repellant core region disposed at least inside the middle part of the absorbent body.

9. The tampon according to claim 1, wherein the absorbent material is fibrous material having a total weight of between 2 g and 0.2 g.

10. The tampon according to claim 1, wherein the absorbent body is provided with a cavity and has an opening to the cavity in a region of the distal end of the absorbent body.

11. The tampon according to claim 1, further comprising a central or core region inside of the absorbent body, wherein the extractor is connected directly to the absorbent body or is connected to the absorbent body via the central or core region.

12. The tampon according to claim 1, wherein an outer surface of the absorbent body or of the middle part is at least partially provided with a casing.

13. The tampon according to claim 1, wherein the proximal end and the middle part are provided with an at least partially liquid-permeable casing.

14. The tampon according to claim 12, wherein the casing comprises a net or a perforated film.

15. The tampon according to claim 1, wherein the absorbent material is fibrous and is selected from the group consisting of rayon, cotton, cellulose, cellulose wadding, layered tissue, sphagnum, bamboo, and chemically reinforced, modified or cross-linked cellulose fibers.

16. The tampon according to claim 1, wherein the absorbent material is fibrous and is a synthetic material selected from the group consisting of polyester fibers, polyolefin fibers, absorbent foams, absorbent sponges, absorbent polymers, capillary channel fibers, synthetic fibers, predominantly open-celled flexible polyurethane foam, fibers of rayon, filaments of rayon, and fibers of a structure type of the crystal modification of cellulose II.

17. The tampon according to claim 1, wherein the absorbent body has, a core region having a diameter inside a bounding circle or inside a bounding cylinder across a length of the core region, the diameter being less than 4 mm.

18. The tampon according to claim 1, wherein the absorbent material is fibrous, wherein the absorbent body has a core region, wherein the absorbent material in the core region is compressed to a first degree, wherein the absorbent material in the other regions of the absorbent body is compressed to a second degree, and wherein the first degree is greater than the second degree.

19. The tampon according to claim 1, wherein the proximal end is of a round or rounded design.

20. The tampon according to claim 1, wherein the proximal end is provided with a cone, and wherein the cone increases in diameter in a direction toward the distal end.

21. The tampon according to claim 1, wherein the absorbent body has a longitudinal direction and is provided with recesses and grooves extending in the longitudinal direction.

22. The tampon according to claim 21, wherein the absorbent body has a longitudinal mid-axis, and
wherein the recesses and the grooves extend in the direction of the longitudinal mid-axis in a wave-shape.

23. The tampon according to claim 21, wherein the grooves and the recesses extend in a spiral shape or helically.

24. The tampon according to claim 21, wherein several of the grooves and recesses are distributed around the absorbent body in a circumferential direction.

* * * * *